US010969332B2

(12) United States Patent
Neugebauer et al.

(10) Patent No.: US 10,969,332 B2
(45) Date of Patent: Apr. 6, 2021

(54) COMBINED OPTICAL-SPECTROSCOPIC METHOD FOR IDENTIFYING MICROBIAL PATHOGENS

(71) Applicants: LEIBNIZ-INSTITUT FÜR PHOTONISCHE TECHNOLOGIEN E.V., Jena (DE); UNIVERSITÄTSKLINIKUM JENA, Jena (DE)

(72) Inventors: Ute Neugebauer, Jena (DE); Jürgen Popp, Jena-Kunitz (DE); Ondrej Stranik, Jena (DE); Bettina Löffler, Jena (DE)

(73) Assignees: LEIBNIZ-INSTITUT FÜR PHOTONISCHE TECHNOLOGIEN E.V., Jena (DE); UNIVERSITÄTSKLINIKUM JENA, Jena (DE)

( * ) Notice: Subject to any disclaimer, the term of this patent is extended or adjusted under 35 U.S.C. 154(b) by 207 days.

(21) Appl. No.: 16/320,825

(22) PCT Filed: Jul. 26, 2017

(86) PCT No.: PCT/IB2017/054533
§ 371 (c)(1),
(2) Date: Jan. 25, 2019

(87) PCT Pub. No.: WO2018/020433
PCT Pub. Date: Feb. 1, 2018

(65) Prior Publication Data
US 2019/0162655 A1 May 30, 2019

(30) Foreign Application Priority Data
Jul. 26, 2016 (DE) .......................... 102016113748.0

(51) Int. Cl.
*G01N 21/31* (2006.01)
*C12Q 1/18* (2006.01)
(Continued)

(52) U.S. Cl.
CPC ............. *G01N 21/31* (2013.01); *C12Q 1/025* (2013.01); *C12Q 1/18* (2013.01); *G01J 3/10* (2013.01);
(Continued)

(58) Field of Classification Search
CPC ....... G01J 3/44; G01N 21/65; G01N 21/6458; G01N 21/6486; C12Q 1/18; G02B 21/00; G02B 21/0076; G16B 40/00
See application file for complete search history.

(56) References Cited

U.S. PATENT DOCUMENTS

| 5,573,927 A | 11/1996 | Nelson |
| 7,428,045 B2 | 9/2008 | Stewart et al. |

(Continued)

FOREIGN PATENT DOCUMENTS

WO 2007056568 A2 5/2007

OTHER PUBLICATIONS

Biao Han, Effects of dietary Bacillus licheniformis on growth performance, immunological parameters, intestinal morphology and resistance of juvenile Nile tilapia (*Oreochromis niloticus*) to challenge infections Jun. 21, 2015 (Year: 2015).*
(Continued)

*Primary Examiner* — Maurice C Smith
(74) *Attorney, Agent, or Firm* — Hunton Andrews Kurth LLP (57) ABSTRACT

Exemplary methods can be provided for the determination of a microbial pathogen. In addition, exemplary methods can be provided for the determination of a microbial pathogen and its anti-infective resistance. Further, an exemplary
(Continued)

method can be provided for determining a bacterium and its antibiotic resistance. Systems and computer-accessible media can be provided for the determination of a microbial pathogen and its anti-infective resistance.

20 Claims, 4 Drawing Sheets

(51) Int. Cl.
| | |
|---|---|
| *G01J 3/44* | (2006.01) |
| *G01N 21/65* | (2006.01) |
| *G16H 10/40* | (2018.01) |
| *C12Q 1/02* | (2006.01) |
| *G01J 3/10* | (2006.01) |
| *G01N 21/64* | (2006.01) |
| *G16B 40/00* | (2019.01) |

(52) U.S. Cl.
CPC ............ *G01J 3/44* (2013.01); *G01N 21/6458* (2013.01); *G01N 21/6486* (2013.01); *G01N 21/65* (2013.01); *G16H 10/40* (2018.01); *G16B 40/00* (2019.02)

(56) References Cited

U.S. PATENT DOCUMENTS

| | | |
|---|---|---|
| 7,548,310 B2 | 6/2009 | Gardner, Jr. et al. |
| 8,547,550 B2 | 10/2013 | Carpenter |
| 8,553,732 B2 | 10/2013 | Maier et al. |
| 2005/0052645 A1 | 3/2005 | Stewart et al. |
| 2005/0123917 A1 | 6/2005 | Labischincki et al. |
| 2007/0086004 A1 | 4/2007 | Maier et al. |
| 2011/0143332 A1 | 6/2011 | Lin et al. |
| 2012/0135454 A1* | 5/2012 | Walsh ................ G01N 21/3563 435/34 |
| 2013/0201469 A1* | 8/2013 | Treado .................. G01N 21/65 356/39 |
| 2014/0278136 A1* | 9/2014 | Shamsheyeva .......... G16B 5/00 702/19 |
| 2014/0377795 A1 | 12/2014 | Gannot et al. |
| 2016/0177366 A1* | 6/2016 | Auner .................... G01N 21/65 435/5 |
| 2018/0355399 A1* | 12/2018 | Novelli Rousseau ... C12Q 1/18 |

OTHER PUBLICATIONS

Schroder, Ulrich-Christian et al., "Combined Dielectrophoresis-Raman Setup for the Classification of Pathogens Recovered from the Urinary Tract," Anal. Chem., vol. 85, No. 22, pp. 10717-10724, Oct. 14, 2013.

The translation Written Opinion of the International Searching Authority dated Nov. 27, 2017 for International Application No. PCT/IB2017/054533.

\* cited by examiner

E. coli strain untreated, after 180 min

4B

E. coli strain, 180 min treated with piperazillin/tazobactam

4C

E. coli 180 min, without antibiotics

4D e. coli with piperazillin/tazobactam after 180 min --> resistent

Fig. 4

COMBINED OPTICAL-SPECTROSCOPIC METHOD FOR IDENTIFYING MICROBIAL PATHOGENS

CROSS REFERENCE TO RELATED APPLICATION(S)

This application relates to, and claims the benefit and priority from International Patent Application No. PCT/IB2017/054533 filed on Jul. 26, 2017 that published as International Patent Publication No. WO 2018/020433 on Feb. 1, 2018, which claims the benefit and priority from German Patent Application No. 10 2016 113 748.0 filed on Jul. 26, 2016, the entire disclosures of which are incorporated herein by reference in their entireties.

FIELD OF THE DISCLOSURE

The present disclosure relates to methods for the determination of a microbial pathogen. In addition, the present disclosure is directed to methods for the determination of a microbial pathogen and its anti-infective resistance. In particular, the present disclosure relates to a method for determining a bacterium and its antibiotic resistance.

BACKGROUND INFORMATION

The currently established techniques for phenotypic resistance testing from patient materials can be based on at least two culturing steps, and thus, the analysis result can be available at the earliest 48 hours after sampling. The first culturing step in this process can be to obtain a pure bacterial culture, the second involves resistance testing itself. Common tests for resistance testing can include the agar diffusion test, the Etest and the microdilution test. The identification of antibiotic resistance by Raman spectroscopy was shown for vancomycin-resistant enterococci (see, e.g., Schröder et al., Scientific Reports, 2015). Further, certain algorithms exist that record the morphology of bacteria under the influence of antibiotics. However, these algorithms require the prior identification of the bacteria and in tests with several clinical isolates showed an error rate of almost 10% (see, e.g., Choi et al., Science Translational Medicine, 2015).

Automated assays likely require larger amounts of biological material to be obtained by overnight culturing. In addition, the diagnosis often takes 8 to 10 hours, or in some cases even longer. Newer approaches based on genotypic identification and characterization of antibiotic resistance can be significantly faster and can often be performed directly from patient material, although they require precise knowledge of characteristic nucleic acid sequences and therefore often fail to identify rapidly mutating multi-resistant Gram-negative pathogens.

Therefore, it is not possible to perform a fast and reliable antibiotic resistance analysis of unidentified microbial pathogens such as bacteria with previous techniques. In order to optimally tailor anti-infective therapy, in particular antibiotic therapy, to the patient and his microbial pathogen, shorter determination times, in particular of antibiotic resistance, would be desirable. In addition, the use of broad-spectrum antibiotics could be reduced and wrong therapies for unknown resistances avoided.

Thus, there may be a need to address and/or resolve at least some of the deficiencies and/or issues present in the prior procedures and/or methods.

OBJECT(S) OF THE PRESENT DISCLOSURE

One of the objects of the present disclosure is to provide a method for a determination of a microbial pathogen. In particular, according to the exemplary embodiments of the resent disclosure, it is preferable to provide a method for a simultaneous determination of a microbial pathogen and its anti-infective resistance. In particular, it is a further object of the present disclosure to provide a method to simultaneously determine a bacterium and its antibiotic resistance.

SUMMARY OF EXEMPLARY EMBODIMENT(S)

According to the exemplary embodiment of the present disclosure, a method can be provided for a determination of a microbial pathogen comprising e.g., using Raman spectroscopy of a sample comprising at least one microbial pathogen, and utilizing an optical detection of the sample. For exemplary, the exemplary method can be used for the determination of a microbial pathogen, comprising:
  determining the Raman spectrum of the microbial pathogen by Raman spectroscopy,
  determining the morphology of the microbial pathogen by optical detection,
  determining the microbial pathogen based on the Raman spectrum and the morphology of the microbial pathogen.

According to a further exemplary embodiment of the present disclosure, the procedure can also comprise determining the anti-infective resistance of the microbial pathogen based on the Raman spectrum and the morphology of the microbial pathogen, whereas the sample further comprises an anti-infective.

An optical detection can be performed by microscopy, holographic detection and/or dynamic light scattering. In certain exemplary embodiments, optical detection can be performed by microscopy. The exemplary microscopic procedure can be, for example, transmitted light microscopy or fluorescence microscopy. Transmitted light microscopy can be used as an exemplary microscopic method.

For example, during the determination of the morphology of the microbial pathogen by optical detection, quantitative morphology parameters can be determined. Accordingly, the determination of the microbial pathogen can be based on the Raman spectrum and the quantitative morphology parameters of the microbial pathogen.

By combining of the optical-morphological determination and the Raman spectroscopic determination, a fast and reliable determination of the microbial pathogen can be facilitated. The identification of the microbial pathogen and, if necessary, its anti-infective resistance can be performed using an automated analysis, e.g., using multivariable statistical methods and comparison with databases that are available locally or centrally.

Such exemplary procedure can facilitate the determination of the microbial pathogens and their antibiotic resistance in a short time using a small number of microbial pathogens. Within a very short time and with a small number of pathogens, the resistance level and/or the minimum inhibitory concentration of an anti-infective agent for the (to be determined) microbial pathogen can be determined. On the basis of the information obtained, the therapy can be specifically adapted to the specific pathogen.

The minimum inhibition concentration can be the concentration at which a threshold value (e.g., band ratio in the Raman spectra or certain extent of morphological change or certain reduction of bacterial growth compared to the untreated sample) is not reached or not exceeded. By comparing the minimum inhibitory concentration determined in this manner with the sensitivity limit values (e.g., according to the EUCAST guideline), the unknown microbial pathogens to be characterized can be classified in the resistance levels, e.g., sensitive, intermediate or resistant.

The terms "determining", "determination" and "identification" may be used interchangeably in the present disclosure.

According to an exemplary embodiment of the present disclosure, a method can be provided for determining the microbial pathogen and its anti-infective resistance, e.g., comprising using the Raman spectroscopy of and/or for a sample comprising at least one microbial pathogen and an anti-infective and optical detection of the sample, and determining the anti-infective resistance based on the Raman spectrum and morphology of the microbial pathogen. The exemplary method can also be used to determine the cell growth of the microbial pathogen by optical detection, whereas the determination of anti-infective resistance can be based on the determined Raman spectrum, the determined morphology and the determined cell growth of the microbial pathogen.

According to a further exemplary embodiment of the present disclosure, when determining the anti-infective resistance of the microbial pathogen, a first indicator of the resistance of the microbial pathogen to the anti-infective agent can be used, whereas the first indicator of the resistance of the microbial pathogen to the anti-infective agent can be or include an unchanged cell morphology of the microbial pathogen compared to negative control data. Further, when determining the anti-infective resistance of the microbial pathogen, a second indicator of the resistance of the microbial pathogen to the anti-infective agent can be used, whereas the second indicator for the resistance of the microbial pathogen to the anti-infective agent can be or include an unchanged Raman spectrum of the microbial pathogen or a Raman spectrum of the microbial pathogen characteristically altered for a particular resistance mechanism, as compared to negative control data. In addition, a third indicator of resistance of the microbial pathogen to the anti-infective agent can be used, e.g., each determining the anti-infective resistance of the microbial pathogen, the third indicator of resistance of the microbial pathogen to the anti-infective agent being an unchanged or slightly unchanged cell growth of the microbial pathogen compared to negative control data.

The negative control data may be data from a sample containing the microbial pathogen without anti-infective agent. The data of this sample may already be available, e.g., as data of a sample which has already been analyzed at an earlier stage according to the exemplary method. Alternatively or in addition, the sample can be analyzed with the microbial pathogen without anti-infective agent in parallel to the sample with the anti-infective agent. In another exemplary embodiment of the present disclosure, the negative control data can originate from the same sample before it has come into contact with the anti-infective.

According to yet another exemplary embodiment of the present disclosure, the exemplary method can be provided for determining a microbial pathogen and its anti-infective resistance in a sample comprising the microbial pathogen and an anti-infective agent comprising, e.g., cultivating the sample comprising at least one microbial pathogen and an anti-infective, determining the Raman spectrum of the microbial pathogen by Raman spectroscopy of the sample under at least two different anti-infective conditions, and determining the morphology of the microbial pathogen by optical detection of the sample under at least two different anti-infective conditions.

According to still another exemplary embodiment of the present disclosure, a method can be provided for determining a microbial pathogen and its antiinfective resistance comprising, e.g., cultivating a sample comprising at least one microbial pathogen and one antiinfective; using Raman spectroscopy of the sample at at least two time points during cultivation of the sample; and utilizing an optical detection of the sample at at least two time points during cultivation of the sample.

For example, the expression of "under at least two different anti-infective agents conditions" in the context of at least some of the exemplary embodiments of the present disclosure can indicate that the sample is exposed to either a different anti-infective concentration and/or a different duration of action of the anti-infective. In one exemplary embodiment, the sample can be divided into two or more aliquots (parts), with a different concentration of anti-infective added to each aliquot. This can indicate that no antiinfective is added to one unit of the sample while a certain concentration of anti-infective is added to another unit. After the duration of action of the anti-infective, the measurement can take place at any time point after the anti-infective has taken effect. The anti-infective's duration of action or persistency can be, e.g., about 5 min, 10 min, 15 min, 20 min, 30 min, 40 min, 45 min, 50 min, 60 min, 70 min, 80 min, 90 min, 120 min or longer. The person skilled in the art can certainly understand and determine the duration of action of anti-infectives.

In another exemplary embodiment of the present disclosure, the Raman spectrum and the morphology of the sample can be determined at at least two time point, e.g., at least one earlier time at which the anti-infective has not yet been added or at which the anti-infective has not yet been able to take effect, and at least one later time at which the anti-infective has taken effect is measured.

According to still another exemplary embodiment of the present disclosure, the anti-infective is not yet added to the earlier time point. Alternatively or in addition, the anti-infective can be added at the earlier time point, and can have a shorter duration of action to the sample at the earlier time point than at the later time point. The earlier time for determining the Raman spectrum and morphology of the sample can be, for example, about 5 min after anti-infective addition or earlier, preferably about 3 min after anti-infective addition or earlier, more preferably about 2 min after anti-infective addition or earlier, particularly preferably about 1 min after anti-infective addition or earlier or before anti-infective addition. The subsequent time point in time can be, for example, after approx. 10 min, 15 min, 20 min, 30 min, 40 min, 45 min, 50 min, 60 min, 70 min, 80 min, 90 min, 120 min or longer after anti-infective addition.

The exemplary combination of optical-morphological and Raman spectroscopic analyses can facilitate the simultaneous identification of the microbial pathogen, as well as the determination of anti-infective resistance in one test. In addition, the combined exemplary method can facilitate a faster and at the same time more sensitive resistance testing. The exemplary method can be relatively easy to parallelize, and can therefore be used in routine diagnostics for testing several anti-infectives (resistogram), in particular antibiotics. For this exemplary method, small amounts of microbial pathogens, such as, e.g., 100-1000 bacteria per test, can be sufficient. Therefore, time-consuming cultivation and isolation procedures can be avoided.

The exemplary combination of optical detection and Raman spectroscopy may serve to locate the microorganisms, and both techniques can also provide important information for the determination of the microbial pathogen and/or its antibiotic resistance. This can mean that not only data from Raman spectroscopy, but also morphological parameters determined by optical detection are used to determine the microbial pathogen and/or its antibiotic resistance. Optical detection can therefore not only used to determine the local position of the microbial pathogen.

For example, according to still further exemplary embodiments of the present disclosure, methods can be provided for determining a microbial pathogen and its anti-infective resistance in a sample comprising the microbial pathogen and an anti-infective comprising, e.g., cultivating the sample comprising at least one microbial pathogen and one anti-infective, determining the Raman spectrum of the microbial pathogen by Raman spectroscopy of the sample under at least two different anti-infective conditions, determining the morphology of the microbial pathogen by optical detection of the sample under at least two different anti-infective conditions, determining the microbial pathogen based on the Raman spectrum and the morphology of the microbial pathogen, and determining the anti-infective resistance of the microbial pathogen based on the Raman spectrum and the morphology of the microbial pathogen.

In additional exemplary embodiment of the present disclosure, methods can be provided for determining a bacterium and its antibiotic resistance comprising, e.g., culturing a sample comprising at least one bacterium and an antibiotic; using Raman spectroscopy of the sample at at least two time points during cultivation of the sample; and utilizing the optical detection of the sample at at least two time points during cultivation of the sample. In particular, using such exemplary embodiments, it is possible to identify a multi-resistant Gram-negative bacterium and its antibiotic resistance. Therefore, the exemplary methods of the present disclosure can be more beneficial than molecular biological methods based on the determination of certain resistance genes. The prior methods have not yet been able to reliably detect the multi-resistant Gram-negative pathogens (MRGN) with their high genetic variability that are currently on the increase. Further, using the exemplary embodiments of the present disclosure, it is possible to identify a fungus and of determining its antifungal resistance.

Typically, Raman spectroscopy takes place at single cell level. This can mean that Raman spectroscopy can be carried out on individual microbial pathogens after a wide field scan in which the individual microbial pathogens can be detected by image recognition procedures. Alternatively or in addition, Raman spectroscopy can be performed on several bacteria in the image field simultaneously. For the identification of mixed infections, segregation procedures can be used.

Optical detection can be used both in the wide field to determine the number of microbial pathogens in the sample and at the single cell level to determine the cell morphology of the microbial pathogen. In order to be able to reliably detect the morphology of the microbial pathogen in the fluid, inhomogeneous electric fields can be used to align the dielectric micro-organisms in the E-field. This exemplary orientation can reduce the random arrangement of microorganisms. In particular, for non-round pathogens (e.g., rods) this can be of interest by simplifying the data analysis, and reducing the number of microorganisms at least optically detected for a certain accuracy.

In one exemplary embodiment of the present disclosure, the Raman spectrum can be measured at different time points during cultivation, and thus information about the biochemical fingerprint of the microbial pathogen is obtained. This can facilitate the determination of the effect of the anti-infective to be determined, e.g., a successful inhibition/killing by the anti-infective or induction of various resistance mechanisms. Thus, the exemplary combination of the Raman spectroscopy procedure and an optical-morphological analysis can facilitate the effective determination of the microorganism (identification), the determination of the number of microbial pathogens in the sample, the determination of whether resistance is present and the mechanism of action of antibiotic resistance.

In the current state of the art, there is no procedure that can provide this information within a short time (a few hours) from the smallest sample material (few bacteria in suspension).

In further exemplary embodiments of the present disclosure, the method may additionally be performed with a control sample containing at least the one microbial pathogen but no anti-infective, e.g., an antibiotic. For example, the procedure can also be performed with several samples containing at least one microbial pathogen and a different anti-infective such as an antibiotic. Alternatively or additionally, the exemplary method can be performed in several samples, each containing at least one microbial pathogen and one anti-infective in a different concentration, in order to obtain quantitative information on the minimum inhibitory concentration (MIC). In addition, an antibiotic-sensitive test strain can be used as an additional control sample. The same antibiotic compounds can be added to the samples with the antibiotic-sensitive test strain in the same concentrations as in the samples with the microbial pathogen to be tested.

The optical detection can take place at the beginning of cultivation and at intervals of not more than about 60 minutes, preferably not more than about 30 minutes, more preferably not more than about 15 minutes, and particularly preferably not more than about 5 minutes. Raman spectroscopy can be performed at the beginning of cultivation and at intervals of maximum 60 minutes, preferably maximum 30 minutes. With the exemplary method, the determination of the microbial pathogen and its anti-infective resistance can be completed within about 180 minutes, preferably about 150 minutes, more preferably less than about 120 minutes, and most preferably less than about 60 minutes.

For example, the method can refer to the identification of pathogenic microbial pathogens. Therefore, the sample can be obtained from an individual, preferably a mammal, particularly preferably a human. The sample can be be a body fluid such as a urine sample or a microcolony transferred into a medium.

For the methods according to the exemplary embodiments of the present disclosure, e.g., only 50 to 1000, preferably 100 to 1000, microbial pathogens are required in one sample. Typically, a sample contains $5 \times 10^1$ to $1 \times 10^5$ preferably $1 \times 10^2$ to $1 \times 10^5$, more preferably $5 \times 10^2$ to $1 \times 10^5$ microbial pathogens. In further exemplary embodiments, the sample can contain $1 \times 10^3$ to $1 \times 10^4$ microbial pathogens.

In one exemplary embodiment, an electric inhomogeneous field can be generated in the sample chamber.

According to a still further exemplary embodiment of the present disclosure, a system can be provided for determining a microbial pathogen, comprising a Raman spectrometer to provide a Raman spectrum of the microbial pathogen, and a device for optical detection of the microbial pathogen to provide optical data of the microbial pathogen. The system can be arranged to determine (i) the morphology of the microbial pathogen by analyzing the optical data and (ii) the microbial pathogen based on a combination of the Raman spectrum and the morphological data of the microbial pathogen.

In another exemplary embodiment, the system can also be configured to determine anti-infective resistance on a combination of the specific Raman spectrum and the specific morphology of the microbial pathogen. By using different anti-infective concentrations, the minimum inhibitory concentration of the pathogen can also be determined. For this exemplary purpose, anti-infective concentrations around the clinical breakpoint (e.g., from EUCAST guidelines) can be used.

In yet another exemplary embodiment, the system can additionally comprise a device which can generate an inhomogeneous electric field in a sample to be determined. Such device can include electrodes, for example. The field strength can be individually adapted to the sample, the chamber and the electrode geometry, and can be between about 2 and 60 V. If there is no active movement for heat dissipation and the sample chamber material is poorly heat conductive, about 16 V should not be exceeded to avoid heating effects.

According to another aspect of the present disclosure, a computer-accessible medium can be provided which can include a computer program which, when executed by a computer processor, can configure the computer processor to determine a pathogen that using exemplary procedures comprising determining a morphology of the microbial pathogen based on the data of a device for optical detection of the pathogen, and determining the microbial pathogen based on a Raman spectrum of the microbial pathogen and the morphology of the microbial pathogen. Further, the computer processor can be configured to determine the anti-infective resistance of the microbial pathogen based on the Raman spectrum and the morphology of the microbial pathogen.

According to another aspect of the present disclosure, a computer-accessible medium can be provided which can include a computer program which, when executed by a computer processor, can configure the computer processor to determine a Raman spectrum of the microbial pathogen based on spectroscopic data from a Raman spectrometer, determining a morphology of the microbial pathogen based on the data of a device for optical detection of the pathogen, and determining the microbial pathogen based on the Raman spectrum and the morphology of the microbial pathogen. In another exemplary embodiment, the computer processor can be configured to determined the anti-infective resistance of the microbial pathogen based on the Raman spectrum and the morphology of the microbial pathogen.

In order to facilitate the optical recording of morphology, the sample chamber may contain electrodes, which can generate an inhomogeneous electric field and thus exert a force on the microorganisms contained in the sample. By this force microbial pathogens are driven into a certain orientation and/or enriched on certain regions of the measuring chip. The anti-infective can have an influence on the polarizability of the microorganism. The effect of an electric field on the sample can thus contribute to an enrichment in the detection field, as well as to a differentiation of the microorganism.

BRIEF DESCRIPTION OF THE DRAWINGS

Further exemplary embodiments of the present disclosure are detailed in the description of the Figures, where this description shall not limit the scope of the exemplary embodiments of the present disclosure. The Figures show:

FIG. 1 shows a system for determining a microbial pathogen (1) which has a camera for optical detection. The exciters (5) to be determined are located in a perforated chamber of a hole chamber plate (3) which has a plurality of hole chambers (4). The optical-morphological detection is performed by a camera (2). A white light source (9) illuminates the sample through the objective (8). Laser (6) and dispersive element with detector (7) forming the Raman spectrometer. The excitation light path and the detection light path pass through the objective (8). The detector (7) is used for Raman spectroscopic detection. The calculation unit (10) serves to determine the pathogens and, if applicable, their anti-infective resistance by determining a morphology of the pathogens based on the data of the camera and determining the pathogens (and, if applicable, their anti-infective resistance) based on the Raman spectrum and the morphology of the microbial pathogen.

In accordance with classical microbiological methods, the MHK of this strain was determined to 0.032 µg Ciprofloxacin/ml. Thus this strain is sensitive to ciprofloxacin.

(the order of the spectra for the band at 1485 cm-1 follows the concentrations given on the right, for the Raman band at 1450 cm-1 the order is exactly reversed).

In accordance with classical microbiological methods, the MHK of this strain was determined to 1 µg Ciprofloxacin/ml. This makes this strain ciprofloxacin-resistant.

Enlargement of a section of FIG. 3A (the order of the spectra for the band at 1485 cm-1 follows the concentrations given on the right, for the Raman band at 1450 cm-1 the order is exactly reversed).

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described embodiments without departing from the true scope and spirit of the subject disclosure as defined by the appended claims.

DETAILED DESCRIPTION OF EXEMPLARY EMBODIMENTS

It should be noted that "comprising" does not exclude any other elements or steps and "one" or "one" does not exclude any multiplicity. It should also be noted that features or steps described in the reference to one of the embodiments can also be used in combination with other features or steps of other embodiments described.

In particular, it should be noted that the methods for the determination of a microbial pathogen also refer to the determination of several microbial pathogens, i.e. several different pathogens are contained in one sample or several samples with different pathogens are examined in parallel. Likewise, more than one anti-infective can be added to a sample or several samples can be tested with anti-infectives in parallel. Further, combinations of several pathogens and anti-infectives are also intended.

For example, the terms "spectrum" and "Raman spectrum" can also include multiple spectra.

The present disclosure relates to exemplary embodiments of a method for determining the microbial pathogen comprising the steps of Raman spectroscopy of a sample comprising at least one microbial pathogen and optical detection of the sample.

Another exemplary embodiment of the present disclosure is directed to a method for determining the microbial pathogen and its anti-infective resistance comprising the steps of Raman spectroscopy of a sample comprising at least one microbial pathogen and an anti-infective and optical detection of the sample. According to another exemplary embodiment of the present disclosure, a method can be provided for determining the microbial pathogen and its anti-infective resistance comprising:

cultivation of a sample comprising at least one microbial pathogen and an anti-infective agent;

Raman spectroscopy of the sample at at least two time points during cultivation of the sample; and optical detection of the sample at at least two time points during the cultivation of the sample.

Further exemplary embodiments relate to methods for the determination of a microbial pathogen and its anti-infective resistance comprehensively by, e.g.:

cultivation of a sample comprising at least one microbial pathogen and an anti-infective agent;

determining the Raman spectrum of the microbial pathogen by Raman spectroscopy at at least two time points during cultivation of the sample;

determining the morphology of the microbial pathogen by optical detection at at least two time points during cultivation of the sample; and determining the microbial pathogen and its anti-infective resistance based on the Raman spectrum and the morphology of the microbial pathogen.

A further exemplary embodiment relates to methods for the determination of a microbial pathogen and its anti-infective resistance comprising:

separating the sample comprising at least one microbial pathogen into at least two aliquots;

mixing the individual aliquots with different concentrations of the anti-infective;

cultivation of the aliquot;

determining the Raman spectrum of the microbial pathogen by Raman spectroscopy;

determining the morphology of the microbial pathogen by optical detection; and determining the microbial pathogen and its anti-infective resistance based on the Raman spectrum and the morphology of the microbial pathogen.

Typically, the Raman spectrum and the morphology can be determined after a duration of action of the anti-infective.

For example, the concentrations can be within the sensitivity and resistance limits. For this a person skilled in the art can use the breakpoints of the breakpoint table of the European Committee on Antimicrobial Susceptibility Testing (EUCAST) (http://eucast.org/clinical_breakpoints/) as an example. For example, the concentration used can be be 0.1 times, 0.2 times, 0.3 times, 0.4 times, 0.5 times, 0.6 times, 0.7 times, 0.8 times, 0.9 times, 1 times, 2 times, 4 times, 8 times or higher times the EUCAST breaking point. In one embodiment, the used concentration is 4 times the EUCAST breaking point.

As an internal quality control, the samples can additionally at the time before the addition of the anti-infective or directly after the addition of the anti-infective be examined by Raman spectroscopy and optical analysis.

The term "microbial pathogen" can include microorganisms such as bacteria, archaea and fungal. In particular, the term refers to micro-organisms that are pathogenic to animals, preferably mammals, particularly preferably humans.

In certain exemplary embodiments, the bacterium can be a multi-resistant gram-negative bacterium. Examples of multi-resistant Gram-negative bacteria are Enterobacteriaceae, e.g. *Escherichia coli, Klebsiella pneumoniae, Klebsiella oxytoca, Proteus* spp., *Enterobacter* spp., *Pseudomonas aeruginosa* and *Acinetobacter baumannii.*

The term "anti-infective" can cover compounds that act against microorganisms, i.e., kill the microorganisms or inhibit their growth. The term includes, for example, antibiotics (against bacteria), antivirals (against viruses), antifungals (against fungal) and anthelmintics (against worms). In particular, the term 'anti-infective' covers antibiotics and antifungals. Anti-infectives and antibiotics include β lactams, glycopeptides, polyketides, macrolide antibiotics, aminoglycoside antibiotics, polypeptide antibiotics, quinolones (and fluoroquinolones) and sulfonamides. Antibiotics work for example by inhibiting cell wall synthesis (e.g. penicillin), inhibiting protein biosynthesis (e.g., kanamycin, neomycin and chloramphenicol), inhibiting correct nucleic acid polymerization (e.g., rifampicin and ciprofloxacin).

Therefore, the methods of the exemplary embodiments of the present disclosure can be suitable for the determination of bacteria and their antibiotic resistance. Thus, a sample comprising at least one bacterium and one antibiotic can be subjected to Raman spectroscopy and optical detection. In addition, the methods according to the exemplary embodiments of the present disclosure can be suitable for the determination of fungal and their antifungal resistance, whereas a sample comprises at least one fungus and one antifungal is subjected to Raman spectroscopy and optical detection.

For example, an anti-infective-resistant microorganism can be used for attenuating or completely neutralizing the growth-inhibiting or killing effect. It is possible to use different strategies for this purpose, e.g., modify the target structure of the anti-infective so that the drug can no longer bind, synthesize enzymes that degrade the anti-infective and render it ineffective, synthesize alternative proteins that take over the function of the protein inhibited by the anti-infective or open up alternative metabolic pathways, the inhibited molecule in such a large excess that the anti-infective concentrations present can only block a part of the target structures and the rest is still present, changes in the membrane structure so that the substances do not enter the cell in the first place (reduced uptake) or can be actively pumped out again (e.g., Efflux pumps). Such exemplary changes lead to the fact that the microorganism can continue to grow despite the presence of the anti-infective (resistance), but there are also some morphological and biochemical changes that can be detected optically as well as by Raman spectroscopy. The above-described resistance mechanisms can occur either individually or in combination. By using electrical fields, the changes may be made more easily visible.

Further exemplary embodiments of the present disclosure can be directed to methods for determining a bacterium and its antibiotic resistance comprising:

a cultivation of a sample comprising at least one bacterium and one antibiotic;

a Raman spectroscopy of the sample at at least two time points during cultivation of the sample; and an optical detection of the sample at at least two time points during the cultivation of the sample.

Additional exemplary embodiments of the present disclosure can be directed to methods for determining a bacterium and its antibiotic resistance comprising:

cultivation of a sample comprising at least one bacterium and one antibiotic;

determining the Raman spectrum of the bacterium by Raman spectroscopy at at least two time points during cultivation of the sample;

determining the morphology of the bacterium by optical detection at at least two time points during cultivation of the sample; and determining the bacterium and its antibiotic resistance based on the Raman spectrum and morphology of the bacterium.

Additional exemplary embodiments of the present disclosure can be directed to methods for determining a fungus and its antifungal resistance comprising:

a cultivation of a sample comprising at least one fungus and an antimycotic;

a Raman spectroscopy of the sample at at least two time points during cultivation of the sample; and an optical detection of the sample at at least two time points during the cultivation of the sample.

Still further exemplary embodiments of the present disclosure can be directed to methods for determining a fungus and its antifungal resistance comprehensively:

cultivating of a sample comprising at least one fungus and an antimycotic;

determining the Raman spectrum of the fungus by Raman spectroscopy at at least two time points during cultivation of the sample;

determining the morphology of the fungus by optical detection at at least two time points during cultivation of the sample; and determining the fungus and its antifungal resistance based on the Raman spectrum and morphology of the fungus.

The time intervals between the at least two time points can be defined elsewhere. In certain exemplary embodiments, at least at the first time point (when optical detection and/or Raman spectroscopy takes place) the sample is not yet mixed with the anti-infective. The anti-infective is added before the next time point, for example the second time point (at which optical detection and/or Raman spectroscopy takes place).

An unchanged cell morphology of the microbial pathogen compared to negative control data can be an indicator of resistance of the microbial pathogen to the anti-infective. In addition, unchanged cell growth of the microbial pathogen compared to negative control data may be an indicator of resistance of the microbial pathogen to the anti-infective. In addition, an unchanged Raman spectrum of the microbial pathogen or a Raman spectrum characteristically altered for a particular resistance mechanism compared to negative control data may be an indicator of the resistance of the microbial pathogen to the anti-infective. In other words, in determination of the anti-infective resistance of the microbial pathogen, a first indicator of the resistance of the microbial pathogen to the anti-infective agent may be used, wherein the first indicator of the resistance of the microbial pathogen to the anti-infective agent is an unchanged or resistance mechanism characteristic change in the cell morphology of the microbial pathogen compared to negative control data. In addition, in determining the anti-infective resistance of the microbial pathogen, a second indicator of the resistance of the microbial pathogen to the anti-infective agent may be used, wherein the second indicator of the resistance of the microbial pathogen to the anti-infective agent is an unchanged Raman spectrum of the microbial pathogen or a Raman spectrum of the microbial pathogen characteristically altered for a particular resistance mechanism compared to negative control data. The term "a Raman spectrum characteristically altered for a particular resistance mechanism" can include characteristic spectral changes known to the person skilled in the art. For certain resistance mechanisms a changed amino acid composition of the bacterium can be detected (e.g. VanA, VanB, VanC, VanD, VanE, VanG, especially VanA, VanB and in particular of vancomycin resistance), in the case of other resistance mechanisms an increased production of certain enzymes or the substances cleaved by these enzymes can be detected, e.g. in the case of β-lactam resistance an increased production of β-lactamases or an increased hydrolysis of the β-lactam ring of the β-lactam antibiotics used.

In addition, in determining the anti-infective resistance of the microbial pathogen, a third indicator of the resistance of the microbial pathogen to the anti-infective agent can be used, wherein the third indicator of the resistance of the microbial pathogen to the anti-infective agent is an unchanged cell growth of the microbial pathogen compared to negative control data.

The term "unaltered growth", as used herein, can also include slightly reduced cell growth. This means that cell growth is reduced by less than 10%, less than 5%, less than 3% or less than 1% compared to negative control data. Cell growth is usually determined by observing the cell number over time, i.e. the growth rate. Cell growth can also be detected morphologically, e.g., by counting cells with a morphology typical for cell division.

Conversely, an altered cell morphology of the microbial pathogen compared to negative control data may be an indicator of sensitivity of the microbial pathogen to the anti-infective. In particular, changes in cell morphology that are characteristic of the sensitivity of the microbial pathogen must be taken into account. In certain exemplary embodiments, minor initial shape changes can therefore be neglected. The morphological changes are often characteristic for certain classes of antibiotics. In addition, altered cell growth of the microbial pathogen compared to negative control data may be an indicator of sensitivity of the microbial pathogen to the anti-infective. In addition, a Raman spectrum of the microbial pathogen characteristically altered for sensitivity to the anti-infective agent compared to negative control data may be an indicator for the sensitivity of the microbial pathogen to the anti-infective agent.

The negative control data can originate from a sample containing the microbial pathogen without anti-infective agent. The data of this sample may already be available, e.g. as data of a sample which has already been analyzed at an earlier stage according to the exemplary embodiment of the present disclosure. Alternatively, the sample can be analyzed with the microbial pathogen without anti-infective agent in parallel to the sample with the anti-infective agent. In another exemplary embodiments, the negative control data may originate from the same sample before it comes into contact with the anti-infective. In addition, the negative control data could come from a sample of an anti-infective resistant strain with or without anti-infective agent, in particular from a sample of an anti-infective resistant strain.

A sample of an anti-infective with a microbial pathogen that is sensitive to this anti-infective (comparison pathogen) could serve as a positive control. For example, the comparison pathogen can be from the same genus, especially from the same species of the pathogen to be investigated. For example, the genus and species of the unknown microbial pathogen can be determined directly using the method described here. Then an unchanged cell morphology of the microbial pathogen compared to the positive control data may be an indicator for a sensitivity of the microbial pathogen to the anti-infective. In addition, unchanged cell growth of the microbial pathogen compared to the positive control data may be an indicator of sensitivity of the microbial pathogen to the anti-infective agent. In addition, an unchanged Raman spectrum of the microbial pathogen compared to the positive control data may be an indicator of the sensitivity of the microbial pathogen to the anti-infective.

Optical detection can be performed by microscopy, holographic detection or dynamic light scattering, preferably microscopy. Typically, microscopy is light microscopy. The term "light microscopy" is familiar to person skilled in the art and includes, among others, transmitted light microscopy, reflected light microscopy, fluorescence microscopy, holography, interference contrast microscopy, polarization microscopy and confocal microscopy or combinations thereof. In preferred embodiments, transmitted light microscopy is used for optical detection. In an exemplary embodiment, a confocal microscope can be used in a transmitted light mode.

Therefore, Raman spectrometers with integrated optical detection devices, in particular microscopes such as transmitted light microscopes or confocal microscopes, can be suitable for carrying out the exemplary methods of the present disclosure. In particular, Raman spectrometers with integrated transmitted light and/or fluorescence microscopes (e.g. alpha300 from WiTEC, Ulm, Germany, inVia confocal Raman microscope from RENISHAW, United Kingdom or XploRA™PLUS from HORIBA) are particularly suitable. Such transmitted light and/or fluorescence microscope can be or include a confocal microscope. It can also be advantageous if a white light source is integrated for optical detection. A laser source is required in particular for Raman spectroscopy. The Raman spectrometer can have a detector, a spectrometer and usually at least one filter.

A lens with a high numerical aperture, i.e., with a numerical aperture greater than or equal to 0.8 and preferably greater than or equal to 0.9, is used for single cell analysis.

Alternatively, individual microorganisms can be locally enriched by the use of inhomogeneous electric fields (e.g. by negative dielectrophoresis accumulation of bacteria in the middle of the sample vessel). Subsequently, Raman spectroscopy can be used to obtain mean value spectra of all microbial pathogens in focus.

Raman spectroscopic methods for the determination of anti-infective resistances are known to persons skilled in the art (see, e.g., Schröder et al.). In Raman spectroscopy, a sample can be excited by monochromatic light (e.g., aser). This also produces inelastically scattered light on the sample, the frequency of which differs from that of the stimulating light. These frequency differences, the so-called Raman shift, contain information about the oscillation states of the molecules and thus about the chemical composition of the microorganism.

Typically, Raman spectroscopy determination is performed at single cell level. For this purpose, for example, a wide-field image of the microhole chamber is taken in white light. The individual bacteria are detected by an image recognition algorithm which is coupled to the hardware of the device. These can be approached automatically, for example by moving the sample stage or by moving the optics. The Raman measurement can then be performed on a single bacterium. The signal is optimized in the Z-focus plane. In the pure medium, the effect of optical traps can also be exploited to achieve an optimal focus. With optimal focusing, the background fluorescence of the medium hardly plays a role. Wavelength-modulated excitation can also be used for robust data analysis. If the signal of a single microorganism is too weak, these can also be enriched at certain points in the sample vessel, e.g. over the measuring range (e.g. by using inhomogeneous electrical fields). Accumulation can then take place at previously defined points in the sample vessel, which can be approached automatically. For the optical analysis of the number and morphology, all microorganisms visible in the image field of the microscope are recorded and used for the evaluation. For Raman spectroscopic analysis, the microorganisms accumulated by the effect of the electric field are used. The electrode structure must be adapted to the size of the microorganisms to be examined.

The sample vessel can be the well of a multiwell plate, a perforated chamber, a microcontainer, or the sample area of a measuring chip without restriction.

Optical detection can be used to determine the cell count, growth rate and/or cell morphology of the microbial pathogen in the sample. This makes it possible, for example, to detect morphological changes caused by the influence of the anti-infective. In addition, the optional use of inhomogeneous electric fields makes it easier to visualize changes in polarizability and can thus be used for faster detection of resistances. The directional orientation, which can be achieved by applying an electric field, can also reduce the scattering of the determined optical parameters. This may shorten the duration of the determination of anti-infective resistance.

The term "morphology" refers to parameters that describe the shape of the microbial pathogen, e.g. size, roundness, area, ratio of area to perimeter, ratio of longest extension (length) to shortest extension (width). Preferred parameters are size, roundness and area. Automatic image recognition algorithms can extract these parameters or parameters derived from them (e.g. parameters of Zernike polynomials) from the optical detection data.

To determine the quantitative information on the morphological change, microscopy is performed at single-cell level. For this purpose, a wide-field image in white light is first taken at each time interval and the various bacteria are automatically recognised and characterised by appropriate image recognition algorithms (see above).

Anti-infective resistance is determined by optical detection and Raman spectroscopy. This can mean that the optical detection data, in particular the microscopy image data and the Raman spectra, are used for the evaluation.

Using holographic approaches or dynamic light scattering, averaged data can be captured on the image section. Particularly with holographic approaches, the characteristics of the individual microbes can also be determined by data evaluation.

In addition, the growth rate of the microbial pathogens can be determined. For this purpose, wide-field images are taken at different time points during the cultivation of the sample. Automatic image recognition algorithms determine the number of microorganisms in the sample. The growth rate is determined by the change in the number of microorganisms over time in the sample.

The determination of the microbial pathogen and, if necessary, its anti-infective resistance is carried out by automated analysis using multivariate statistical methods, such as, e.g., main component analysis, neural networks or support vector machines and various correlation procedures. These automated analysis methods can be trained with image data and Raman spectra of different microorganisms (especially bacteria) with different anti-infectives (especially antibiotics). The optical and spectral data are independent, but reflect the same changes in the microorganisms. This increases the accuracy by combining the information. This allows shorter analysis times to be achieved with high accuracy. For the combined evaluation of the spectral information and the image data, two approaches are possible: a quantitative parameters (e.g. number of microbial pathogens, roundness, size, form factor (aspect ratio), etc.) are determined from the image data and added to the Raman data (intensity over wave numbers) for multivariate statistical evaluation; and b. From the Raman data, marker bands are identified by statistical evaluation (specific to the mechanism of action of the anti-infective used) and from the relative intensities of the marker bands individual variables are generated, which can be evaluated together with the quantitative parameters from the optical analysis in a mixed statistical model.

Typically the microorganisms (e.g., bacteria) are used as pure suspension in the exemplary methods of the present disclosure. For this purpose, the microorganisms (e.g., bacteria) are introduced into the chambers of a microwell plate intended for analysis as an aliquot of the suspension. Since the same volume and the same concentration are always required for all chambers, filling can be carried out automatically by appropriate devices. Gravity causes the microorganisms (e.g. bacteria) to sink to the ground. Alternatively, the microorganisms could also be embedded in a suitable embedding medium, e.g., agarose. The corresponding diffusion times of the anti-infective agent must be took into consideration. Alternatively, the pathogen suspension (e.g. bacterial suspension) can be passed through a suitable microfluidic plate.

The terms "micro hole plate" and "microwell plate" can be used interchangeably and refer to titer plates with a filling volume of 0.1 µl to 2000 µl, preferably 0.5 µl to 1000 µl, more preferably 1 µl to 500 µl, even more preferably 2 µl to 200 µl, most preferably 5 µl to 100 µl, for example 10 µl. Micro-hole plates are usually made of plastic. Preferred are micro hole plates with a glass bottom. The bottom may have a thin coating of agarose or poly-L-lysine. This can favour the accumulation of bacteria near the glass bottom. If electrodes are to be used (to generate an inhomogeneous electric field), they are also applied to the bottom plate. An arrangement in the walls of the perforated chambers is also conceivable for the application described here. In preferred designs, perforated chamber plates are used which do not influence the growth of the microbial pathogens. By the use of micro hole plates only little bacterial material is needed. Micro hole plates are inexpensive and therefore suitable for low-cost routine diagnostic applications. The bottom of the chamber of the hole plate should be wetted by the pathogen suspension. The size of the chamber can be adapted to the image field of the microscope used.

For the cultivation of microorganisms, media suitable for the cultivation of a broad spectrum of microorganisms are suitable, such as heart-brain broth (typical composition: calf s brain infusion 12.5 g/l; bovine heart infusion 5.0 g/l; proteose peptone 10.0 g/l; glucose 2.0 g/l; sodium chloride 5.0 g/l; disodium hydrogen phosphate 2.5 g/l; pH 7.4±0.2; e.g. from Carl Roth, Germany).

The microbial pathogens are cultivated at a temperature that is as optimal as possible for the cell division of the pathogen. As a rule, cultivation takes place between 25° C. and 39° C., preferably between 30° C. and 38° C., particularly at 37° C. For continuous temperature maintenance, a sample chamber can be used which is set to the desired temperature, e.g. 37° C. Since Raman spectroscopy and optical detection are performed parallel to cultivation, the sample chamber on or around the Raman spectrometer with integrated optical detection device is arranged in the device so that the sample can be kept at the desired temperature during Raman spectroscopy and optical detection. The temperature fuse can be either local (e.g. by heating foil) or global (includes microhole plate and parts of the optical structure). The light cable can be conducted through optical fibres.

In an exemplary embodiment, the device can have two sample chambers with different temperatures. For example, one sample chamber may be set to 30° C., and the second sample chamber to 37° C. The sample is first introduced into one of the two chambers, for example the 37° C. tempered chamber, and the microbial pathogens are identified by optical detection and/or Raman spectroscopy. If it is known from the identified pathogen that it grows better at 30° C., the microhole plate is inserted into the second chamber. The sample can be introduced into the chamber automatically. Alternatively, a sample chamber could be used and the temperature of the sample chamber adapted to the optimal growth temperature of the pathogen after identification of the microbial pathogen. In a further embodiment, two samples, which are identical with regard to the microbial pathogen and (if applicable) the antibiotic, are cultivated in parallel in two chambers with different temperatures, e.g. in one chamber at 37° C. and one at 30° C.

The exemplary embodiments of the method according to the present disclosure can be used for all anti-infectives (especially antibiotics). For example, a pure sample without anti-infective additive or a pure sample without anti-infective resistance is used as control. Alternatively, comparative data records can be used that are already available for the corresponding pathogen (e.g., comparable pathogen of the same species) in combination with the corresponding anti-infectives. In one embodiment, comparative data sets are used in which the same anti-infective agent is added to the sample to be tested, but the microbial pathogen differs from the sample to be tested. The anti-infective may already be lyophilized in the chambers of the hole plate. Depending on the origin of the sample material (blood culture, respiratory tract, urinary tract etc.) an appropriate cartridge can be selected and filled.

The anti-infective is dosed into the chambers after Raman spectroscopic identification of the germs. For this purpose, storage vessels with injection connections, for example, can be built into the device. In this version, it can be recommended to run a test strain with known sensitivity in a row of chambers in order to simultaneously control the effectiveness of the anti-infective.

In an exemplary embodiment, a large amount of the bacterial suspension (sufficient for the required antibiotic testing plus control) is poured into a central chamber. After Raman spectroscopic identification of the pathogens in the device, a micro hole plate is selected, which contains the relevant antibiotics in the relevant concentrations, and the bacterial suspension is passed microfluidically into the corresponding chambers.

In another exemplary embodiment, the method can be performed with at least one control sample. This control sample may contain at least one microbial pathogen without anti-infective agent. Thereby the growth rate and cell morphology of the sample(s) comprising the microbial pathogen and an anti-infective can be compared with the growth rate and cell morphology of the control sample(s) comprising the microbial pathogen without the anti-infective.

In addition, the exemplary method may be performed in a sample comprising an antiinfectiveasensitive test strain.

In a further exemplary embodiment, the method can be performed on several samples, each containing a microbial pathogen and a different anti-infective. Since the exemplary procedure of the present disclosure can be parallelized, it is thus possible to simultaneously test the resistance of the microbial pathogen against several anti-infectives. This is due to the increasing incidence of multi-resistant microbial pathogens, especially multi-resistant bacteria (e.g., methicillin-resistant Staphylococcus aureus (MRSA), multi-resistant *Clostridium difficile* but also multi-resistant Gram-negative bacteria (MRGN) such as multiresistant *Pseudomonas aeruginosa, Acinetobacter baumannii,* or *Enterobacteria* such as *Escherichia coli* and *Klebsiella pneumoniae*) of enormous importance.

In yet another exemplary embodiment, the method can be carried out on several samples, each containing a microbial pathogen and an anti-infective agent in different concentrations. This makes it easy to determine the minimum inhibitory concentration.

The exemplary embodiments of the present disclosure can also be suitable for the parallel analysis of different anti-infectives in different concentrations.

In additional exemplary embodiments, the optical detection takes place at the beginning of cultivation and at intervals not exceeding 120 minutes, preferably 60 minutes, particularly preferably not more than 30 minutes, more preferably not more than 15 minutes, even more preferably not more than 5 minutes. Raman spectroscopy shall be carried out at the beginning of cultivation and at intervals not exceeding 120 minutes, preferably not exceeding 60 minutes, particularly preferably not exceeding 30 minutes.

Using the exemplary embodiments of the method according to the present disclosure, the determination of the microbial pathogen and its anti-infective resistance can be completed within 180 minutes, preferably 150 minutes, more preferably 120 minutes, especially preferably 60 minutes. Applied technologies for determining the genus and the type of the microbial pathogen can be Raman spectroscopy and for determining the senility of anti-infective a combination of Raman spectroscopy and optical analysis can be used. Identification and resistance determination can be carried out in the same device. No further sample pretreatment steps are necessary. The required sample material is minimal.

For example, the exemplary method can refer to the identification of pathogenic microbial pathogens. Therefore, the sample is taken from an individual, preferably a mammal, particularly preferably a human. The sample may be a body fluid, e.g. a urine sample, or a microcolony transferred into a medium. The urine sample is typically filtered using a filter that separates impurities but allows microbial pathogens to pass through. Complex samples, which usually contain many components, such as blood samples, or also colonizing flora, such as aspirating material, are, as established in microbiological laboratories and known by person skilled in the art, spread out and cultivated for a short time, e.g. less than 6 h, preferably less than 4 h, more preferably less than 3 h, especially preferably less than 2 h. Since only little bacterial material is required, short incubation times of approx. 2-3 h are sufficient to obtain enough sample material. Alternatively, microfluidic purification steps are also conceivable, which make the microbial pathogens directly accessible from the complex patient material for further analysis with the exemplary embodiments described herein. Such a pre-purification can also be directly coupled to the titer plate system described here.

For the methods according to the exemplary embodiments, only 50 to 1000, preferably 100 to 1000, microbial pathogens are required in one sample. Typically a sample contains $5 \times 10^1$ to $1 \times 10^5$ preferably $1 \times 10^2$ to $1 \times 10^5$, more preferably $5 \times 10^2$ to $1 \times 10^5$ microbial pathogens. In particularly preferred designs, the sample contains $1 \times 10^3$ to $1 \times 10^4$ microbial pathogens. Since only a small number of pathogens is necessary both for the determination of the pathogens and for the determination of their anti-infective resistance, one or more preculture steps, which are necessary in the state of the art methods, can be resigned. As these pre-culture steps usually take between 6 and 24 hours, the result can be achieved much faster in the present method after sampling. The duration of the exemplary procedure for determining the pathogens and/or their anti-infective resistance may be reduced accordingly. Thus, the determination of the microbial pathogen and its anti-infective resistance is possible within 180 minutes, preferably 150 minutes, especially preferred 120 minutes after sampling.

A further exemplary embodiment is directed to a method for determining the microbial pathogen and its anti-infective resistance comprising the steps:

cultivation of a sample comprising at least one microbial pathogen and an anti-infective agent;

a cultivation of a control sample comprising at least one microbial pathogen without anti-infective agent;

a Raman spectroscopy of the samples at at least two time points during the cultivation of the sample; and an optical detection of the samples at at least two time points during the cultivation of the sample.

A still further exemplary embodiment is directed a system for determining a microbial pathogen comprising:

a Raman spectrometer to provide spectroscopic data of the microbial pathogen; and a device for optical detection of the microbial pathogen to provide optical data of the microbial pathogen, whereas the system is arranged to determine the morphology of the microbial pathogen by analyzing the optical data and to determine the microbial pathogen based on a combination of the Raman spectrum and the morphological data of the microbial pathogen.

A further exemplary embodiment refers to a system for determining a microbial pathogen comprising:

a Raman spectrometer to provide spectroscopic data of the microbial pathogen; and a device for optical detection of the microbial pathogen to provide optical data of the microbial pathogen, whereas the system is arranged to process a Raman spectrum of the microbial pathogen, to determine the morphology of the microbial pathogen by analysis of the optical data, and to determine the microbial pathogen based on a combination of the Raman spectrum and the morphological data of the microbial pathogen.

In an exemplary embodiment, the system can also be configured to determine anti-infective resistance based on a combination of the specific Raman spectrum and the specific morphology of the microbial pathogen.

Another exemplary aspect of the present disclosure refers to a computer-accessible medium which has a computer program for determining a pathogen that, when executed on a computer processor, configures the computer processor to perform the following procedures:

determining a morphology of the microbial pathogen based on the data of a device for optical detection of the microbial pathogen, and determining the microbial pathogen based on a Raman spectrum and the morphology of the microbial pathogen.

Yet another exemplary aspect of the present disclosure refers to a computer-accessible medium which has a computer program for determining a pathogen that, when executed on a computer processor, configures the computer processor to perform the following procedures:

processing of a Raman spectrum of the microbial pathogen, determining a morphology of the microbial pathogen based on the data of a device for optical detection of the microbial pathogen, and determining the microbial pathogen based on the processed Raman spectrum and the morphology of the microbial pathogen.

The term "processing of a Raman spectrum" covers common methods known to person skilled in the art for signal optimization of the Raman spectrum, such as background correction, normalization or wave number correction.

The computer processor can be configured to determine the anti-infective resistance of the microbial pathogen based on the Raman spectrum and the morphology of the microbial pathogen after interaction with the anti-infective.

For example, the program element can be used to update an existing program element.

In another exemplary embodiment, the computer processor can be configured to determine the anti-infective resistance of the microbial pathogen based on the Raman spectrum and the morphology of the microbial pathogen.

The computer-readable medium can be considered as or include a storage medium, e.g., USB stick, CD or DVD, data storage device, hard disk or any other medium on which a program element as described above can be stored.

Exemplary Embodiment 1

Preparation of a bacterial suspension and introduction into chambers of a microhole chamber plate (filling volume of chamber≤100 aliquot 10 µl): One microhole chamber contains no antibiotic, the other microhole chambers contain one or different antibiotics.

Raman spectroscopic identification of the pathogens by recording individual spectra of several individual pathogens in the measuring chamber and comparing the spectra with a database for determining the type of bacteria: Using appropriate image recognition algorithms, which are coupled to the hardware of the device, different bacteria can be automatically approached. Incubation of the bacteria at 37° C.

Tracking the growth of bacteria with the aid of white light microscopy and subsequent image evaluation: A wide-field image of each hole chamber is taken every approx. 15 minutes. Image recognition algorithms provide quantitative information about morphological changes. In the evaluation, this information is evaluated relative to the control without antibiotic.

Raman spectroscopic characterization: After 60 and 120 minutes, Raman spectroscopic characterization is performed on approximately 10-20 bacteria in the individual chambers. By analyzing the Raman spectra, quantitative information about the biochemical fingerprint, i.e. information about the biochemical composition of the bacteria, is obtained. In the evaluation, this information is determined relative to the control without antibiotic. Based on the image information, the bacteria are automatically approached by the automated procedure of the sample stage.

Automated analysis of antibiotic resistance by integrating data on growth curves, quantitative information on morphological changes, and Raman spectroscopic characterization: Spectral changes of bacterial Raman spectra in the antibiotic-added chambers are compared with those in the control chamber without antibiotic addition. If the changes characteristic of the mechanism of action of the antibiotic occur, this is an indicator of sensitivity. If no differences are detectable or the differences characteristic of a particular resistance mechanism are detectable, this is an indicator of resistance. The comparison is made by statistical evaluation of the (pretreated) Raman spectra using multivariate methods (e.g. main component analysis, linear discriminant analysis, support vector analysis or others). Similarly, indicators of resistance and sensitivity are obtained from the analysis of growth characteristics and morphological changes. These three indicators are used with the aid of a weighted statistical procedure to make statements about the resistance or sensitivity of the examined bacterium to the various antibiotics.

Optical detection is performed on a Raman spectrometer with integrated confocal microscope with white light illumination (e.g. inVia confocal Raman microscope from RENISHAW, United Kingdom or XploRA™PLUS from HORIBA).

Exemplary Embodiment 2

Introduction of aliquots of a bacterial suspension into chambers of a microhole chamber plate (filling volume of the chambers≤100 µl, aliquot 10 µl). Each chamber contains a different concentration of an antibiotic whose resistance is to be tested (concentration range: 0 µg/ml to 4-fold breakpoint according to EUCAST). The chambers are equipped with electrodes that enable the generation of an electric field.

Switch on the electric field. The bacteria are concentrated at a defined point in the perforated chamber. The Raman spectroscopic identification of the pathogens is carried out by recording Raman spectra at the defined position in the measuring chip and comparing the spectra with a database to determine the type of bacteria. The following incubation of the bacteria at 37° C. can take place without the generation of an electric field.

Tracking the growth of bacteria with the aid of white light microscopy and subsequent image evaluation: A wide-field image is taken in each perforated chamber every approx. 5-15 minutes. Image recognition algorithms acquire quantitative information about morphological changes. For enrichment and alignment of the bacteria (especially interesting for rod-shaped bacteria) the electric field can be switched on immediately before the microscope image is taken. The evaluation includes the dynamic change of the optical parameters (and the polarizability, if applicable). As a control both time 0 min and the aliquot without antibiotic are used.

Raman spectroscopic characterization: After 30, 60 and 90 minutes, Raman spectroscopic characterization takes place within the bacterial cloud enriched by the electric field. Several spectra are recorded in each measuring chamber. By analyzing the Raman spectra, quantitative information about the biochemical fingerprint, i.e. information about the biochemical composition of the bacteria, is obtained. Depending on the antibiotic, the evaluation may include the formation of band ratios or multivariate statistical methods compared to the control without antibiotic.

Automated analysis of antibiotic resistance and determination of the minimum inhibitor concentration: For this purpose, both image information and Raman data are evaluated together for each antibiotic concentration. This includes information on bacterial growth, quantitative parameters of morphology as well as characteristic Raman bands. For each concentration of antibiotics, it is determined whether the concentration of antibiotics added was sufficient to inhibit bacterial growth or not. The minimum inhibition concentration is the concentration at which a threshold value (e.g. band ratio in the Raman spectra or certain extent of morphological change or certain reduction of bacterial growth compared to the untreated sample) is not reached or not exceeded. The threshold values are characteristic for certain antibiotic classes and duration of action. By comparing the minimum inhibitory concentration determined in this way with the sensitivity limit values (e.g. according to the EUCAST guideline), the unknown bacteria to be characterised are classified in the resistant levels sensitive, intermediate (defined for some bacterial/antibiotic combinations) or resistant.

Figure 1:
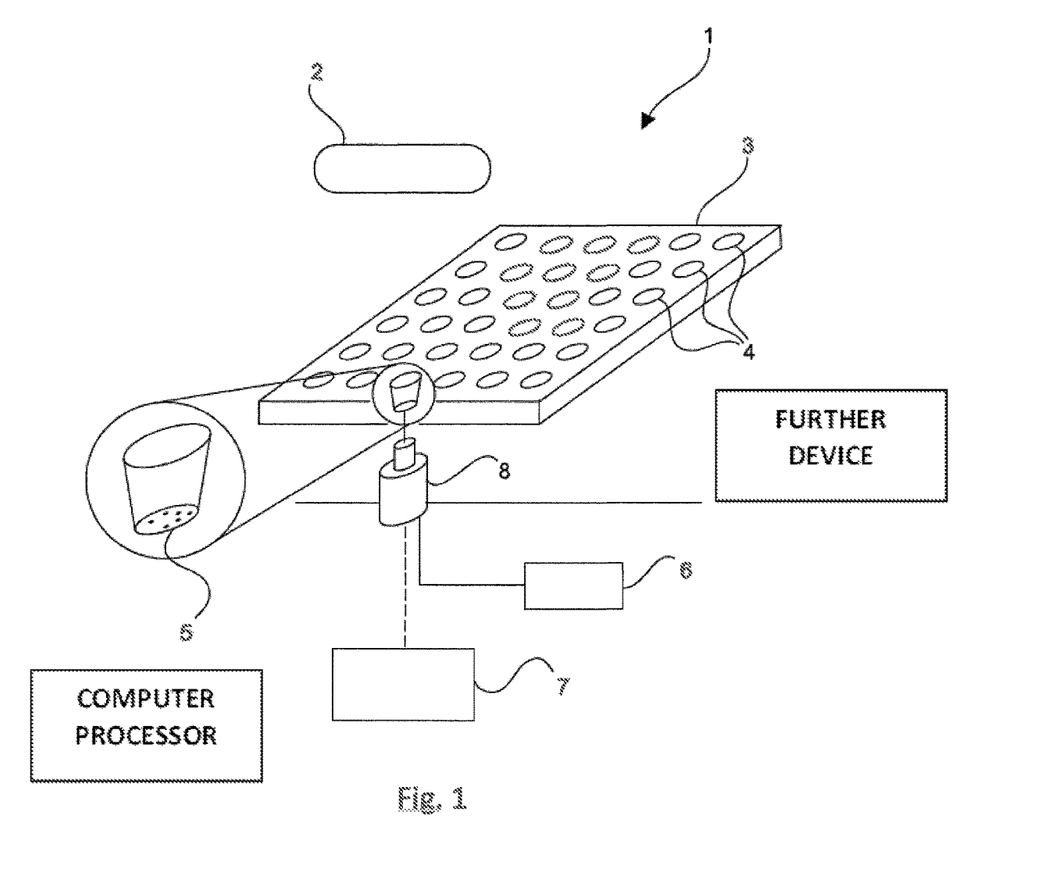
FIG. 1 is a diagram of a system for the determination of a microbial pathogen according to an exemplary embodiment of the present disclosure.

Turning to the figures, FIG. 1 shows a diagram of a system for the determination of a microbial pathogen according to an exemplary embodiment of the present disclosure. In particular, the exemplary system of FIG. 1 is provided for determining a microbial pathogen (1) which has a camera for optical detection. The exciters (5) to be determined are located in a perforated chamber of a hole chamber plate (3) which has a plurality of hole chambers (4). The optical-morphological detection is performed by a camera (2). A white light source (9) illuminates the sample through the objective (8). Laser (6) and dispersive element with detector (7) forming the Raman spectrometer. The excitation light path and the detection light path pass through the objective (8). The detector (7) is used for Raman spectroscopic detection. The calculation unit (10) serves to determine the pathogens and, if applicable, their anti-infective resistance by determining a morphology of the pathogens based on the data of the camera and determining the pathogens (and, if applicable, their anti-infective resistance) based on the Raman spectrum and the morphology of the microbial pathogen.

Figure 2:
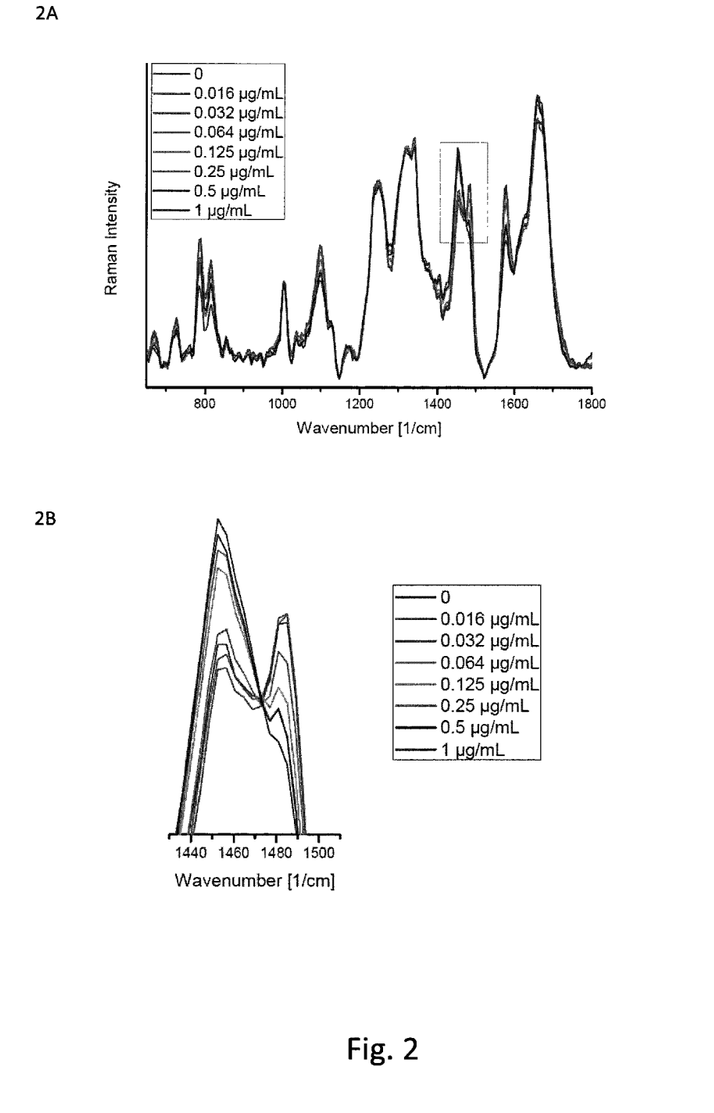
FIG. 2A is an exemplary graph of Raman spectra of an *E. coli* strain after 90 minutes of duration of action to different concentrations of ciprofloxacin.
FIG. 2B is an enraged graph of a particular section of FIG. 2A.

FIG. 2A shows an exemplary graph of Raman spectra of an E. coli strain after 90 minutes of duration of action to different concentrations of ciprofloxacin. In accordance with classical microbiological methods, the MHK of this strain was determined to 0.032 µg Ciprofloxacin/ml. Thus this strain is sensitive to ciprofloxacin. FIG. 2B illustrates an enraged graph of a particular section of FIG. 2A (the order of the spectra for the band at 1485 cm-1 follows the concentrations given on the right, for the Raman band at 1450 cm-1 the order is exactly reversed).

Figure 3:
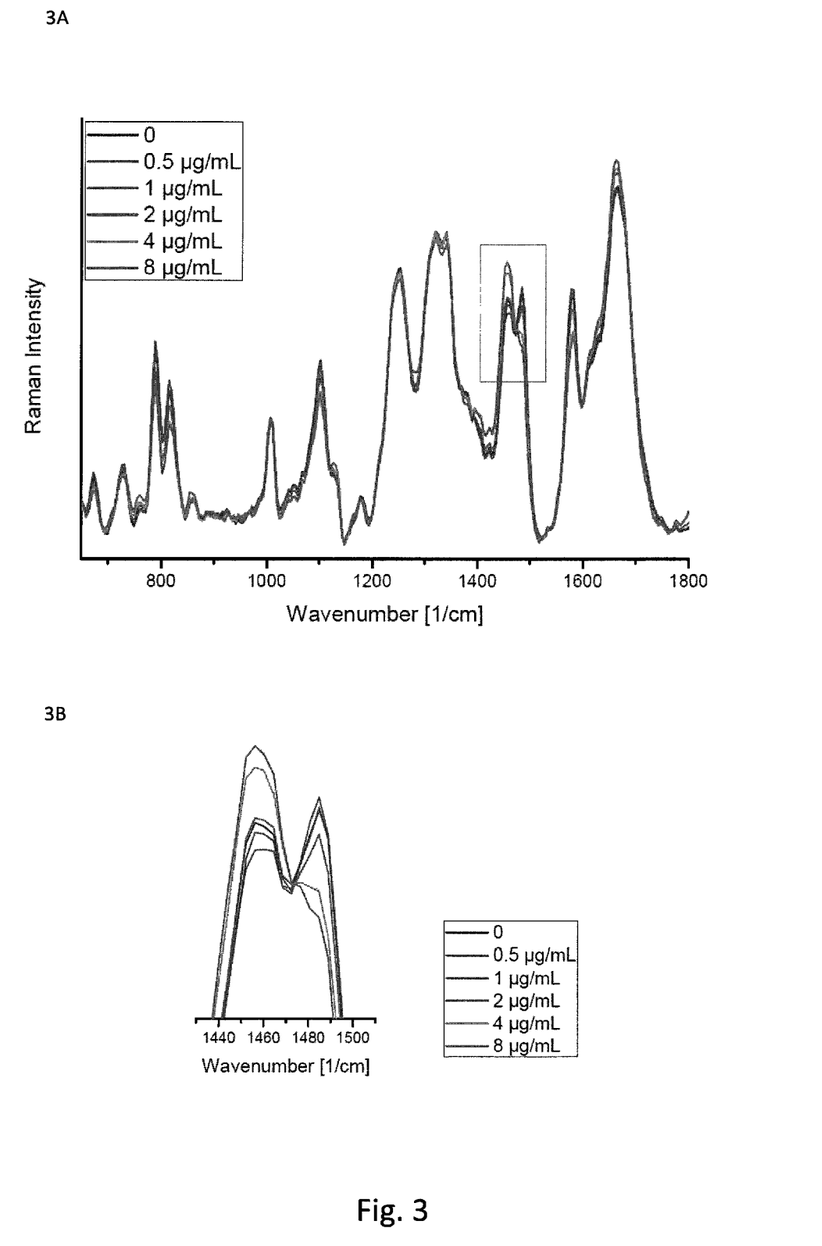
FIG. 3A an exemplary graph of Raman spectra of another *E. coli*-strain after 90 minutes of duration of action to different concentrations of ciprofloxacin.
FIG. 3B is an enraged graph of a particular section of FIG. 2A.

FIG. 3A shows an exemplary graph of Raman spectra of another E. coli-strain after 90 minutes of duration of action to different concentrations of ciprofloxacin. In accordance with classical microbiological methods, the MHK of this strain was determined to 1 µg Ciprofloxacin/ml. This makes this strain ciprofloxacin-resistant. FIG. 3B illustrates an enraged graph of a particular section of FIG. 3A (the order of the spectra for the band at ~1485 cm-1 follows the concentrations given on the right, for the Raman band at 1450 cm-1 the order is exactly reversed).

Figure 4:
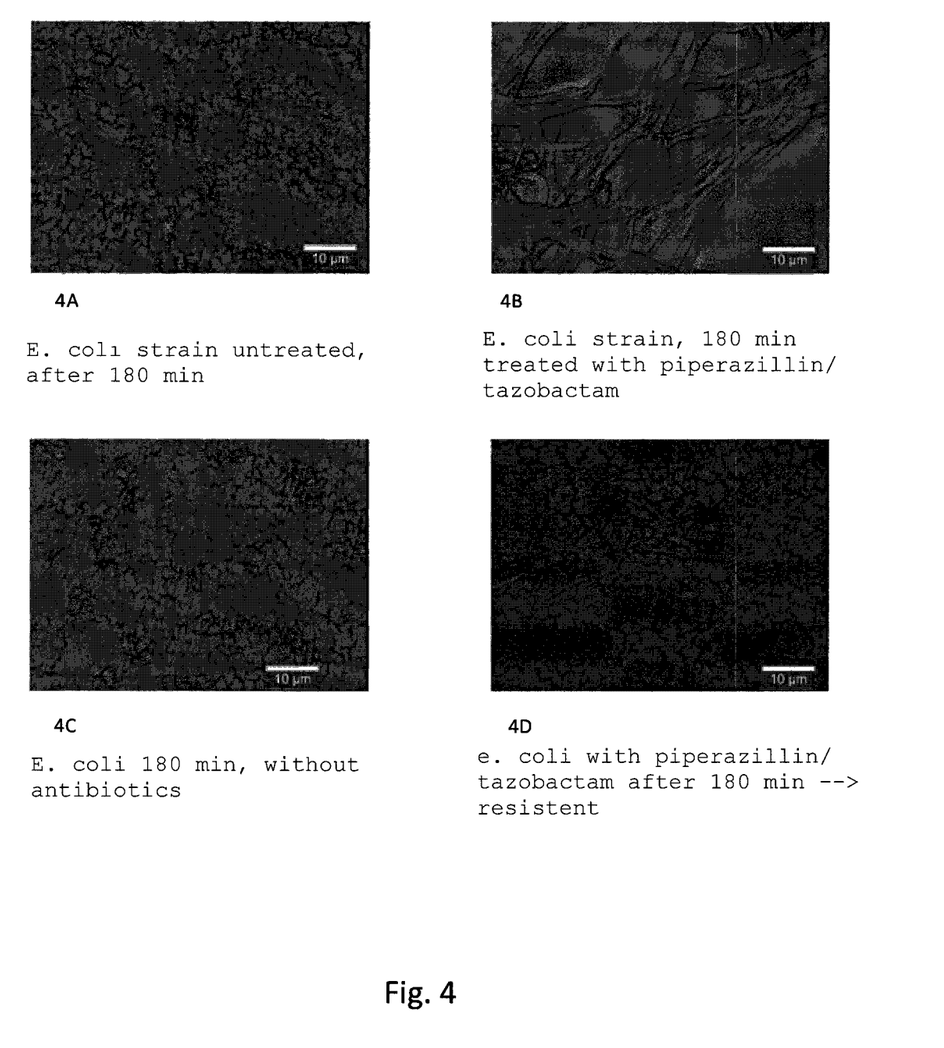
FIG. 4A is an illustration of an exemplary morphology of *E. coli* strains without an antibiotic treatment.
FIG. 4B is an illustration of an exemplary morphology of *E. coli* sensitive strains about 180 min after treatment with piperazilline/azobactam.
FIG. 4C is an illustration of another exemplary morphology of *E. coli* strains without an antibiotic treatment.
FIG. 4D is an illustration of an exemplary morphology of *E. coli* resistive strains about 180 min after treatment with piperazilline/azobactam.

FIGS. 4A and 4C show exemplary illustrations of an exemplary morphology of E. coli strains without an antibiotic treatment. FIG. 4B provides an illustration of an exemplary morphology of E. coli sensitive strains about 180 min after treatment with piperazilline/azobactam. FIG. 4D provides an illustration of an exemplary morphology of E. coli resistive strains about 180 min after treatment with piperazilline/azobactam.

The invention claimed is:

1. A method for determining a microbial pathogen and an anti-infective resistance thereof in a sample comprising the microbial pathogen and an anti-infective, the method comprising:
    cultivating the sample comprising at least one microbial pathogen and an anti-infective agent;
    determining a Raman spectrum of the microbial pathogen by a Raman spectroscopy of the sample under at least two different anti-infective conditions;
    determining a morphology of the microbial pathogen by an optical detection of the sample under the at least two different anti-infective conditions;
    determining the microbial pathogen based on the Raman spectrum and the morphology of the microbial pathogen, and
    determining the anti-infective resistance of the microbial pathogen based on the Raman spectrum and the morphology of the microbial pathogen.

2. The method according to claim 1, wherein the at least two different anti-infective conditions includes at least one of a different anti-infective concentration or a different duration of action of the anti-infective.

3. The method according to claim 1, wherein the Raman spectrum of the microbial pathogen is determined by the Raman spectroscopy at at least two time points during the cultivation of the sample, and wherein the morphology of the microbial pathogen is determined at the at least two time points during the cultivation of the sample.

4. The method according to claim 1, wherein the optical detection is performed by a microscopy, a holographic detection or a dynamic light scattering, and wherein the microscopy is a transmitted light microscopy or a fluorescence microscopy.

5. The method according to claim 1, further comprising determining a cell growth of the microbial pathogen by the optical detection, wherein the determination of the anti-infective resistance is based on the determined Raman spectrum, the determined morphology and the determined cell growth of the microbial pathogen.

6. The method according to claim 1, wherein the at least one microbial pathogen is a bacterium, and the anti-infective agent is an antibiotic.

7. The method according to claim 1, wherein, when determining the anti-infective resistance of the microbial pathogen, a first indicator of the resistance of the microbial pathogen to the anti-infective agent is used, and wherein the first indicator of resistance of the microbial pathogen to the anti-infective agent is an unchanged cell morphology of the microbial pathogen compared to negative control data.

8. The method according to claim 7, wherein, when determining the anti-infective resistance of the microbial pathogen a second indicator of resistance of the microbial pathogen to the anti-infective agent is used, wherein the second indicator for the resistance of the microbial pathogen to the anti-infective agent is an unchanged Raman spectrum of the microbial pathogen or a Raman spectrum of the microbial pathogen characteristically altered for a particular resistance mechanism as compared to negative control data.

9. The method according to claim 7, wherein, when determining the anti-infective resistance of the microbial pathogen a third indicator for the resistance of the microbial pathogen to the anti-infective agent is used, and wherein the third indicator of resistance of the microbial pathogen to the anti-infective agent is an unchanged cell growth of the microbial pathogen compared to negative control data.

10. The method according to claim 7, wherein the negative control data originates from a sample containing the microbial pathogen without anti-infective agent.

11. The method according to claim 1, wherein the method is performed with a control sample containing the at least one microbial pathogen without anti-infective agent.

12. The method according to claim 1, wherein the method lasts less than 180 minutes.

13. The method according to claim 1, wherein the method lasts less than 120 minutes.

14. The method according to claim 1, wherein the sample is taken from an individual.

15. The method according to claim 1, wherein the sample is a mammal.

16. The method according to claim 1, wherein the sample contains $1*10^2$ to $1*10^5$ microbial pathogens.

17. The method according to claim 1, wherein an electric inhomogeneous field is generated in the sample.

18. A system for determining of a microbial pathogen and an anti-infective resistance thereof, comprising:
 a Raman spectrometer configured to provide a Raman spectrum of the microbial pathogen;
 a detector configured to provide an optical detection of the microbial pathogen so as to provide optical data of the microbial pathogen; and
 a computer processor configured to determine (i) the morphology of the microbial pathogen by analyzing the optical data, and (ii) the microbial pathogen based on a combination of the Raman spectrum and the morphology of the microbial pathogen,
 wherein the computer processor is further configured to determine the anti-infective resistance based on a combination of the Raman spectrum and the morphology of the microbial pathogen.

19. The system according to claim 18, further comprising a further device configured to generate an inhomogeneous electric field in a sample to be determined.

20. A computer-accessible media including a computer program element thereon that, when executed on a computer processor, configures the computer processor to perform procedures comprising:
 determining a morphology of a microbial pathogen based on data of a detector for an optical detection of the pathogen; and
 determining the microbial pathogen based on a Raman spectrum of the microbial pathogen and the morphology of the microbial pathogen; and
 determining an anti-infective resistance of the microbial pathogen based on the Raman spectrum and the morphology of the microbial pathogen.

* * * * *